United States Patent
Bertagnoli

(10) Patent No.: US 8,764,834 B2
(45) Date of Patent: Jul. 1, 2014

(54) INTERVERTEBRAL DISK PROSTHESIS

(75) Inventor: Rudolf Bertagnoli, Straubing (DE)

(73) Assignee: Global Medical Consulting GmbH, Bogen (DE)

( * ) Notice: Subject to any disclaimer, the term of this patent is extended or adjusted under 35 U.S.C. 154(b) by 830 days.

(21) Appl. No.: 12/741,353

(22) PCT Filed: Nov. 6, 2008

(86) PCT No.: PCT/DE2008/001829
§ 371 (c)(1),
(2), (4) Date: May 4, 2010

(87) PCT Pub. No.: WO2009/071044
PCT Pub. Date: Jun. 11, 2009

(65) Prior Publication Data
US 2010/0249936 A1    Sep. 30, 2010

(30) Foreign Application Priority Data
Dec. 4, 2007   (DE) .................. 10 2007 058 304

(51) Int. Cl.
*A61F 2/44* (2006.01)

(52) U.S. Cl.
USPC ..................................... 623/17.16

(58) Field of Classification Search
USPC .......................... 623/17.11–17.16
See application file for complete search history.

(56) References Cited

U.S. PATENT DOCUMENTS

| | | | |
|---|---|---|---|
| 5,401,269 A | 3/1995 | Büttner-Janz et al. | |
| 6,039,763 A | 3/2000 | Shelokov | |
| 2003/0078667 A1* | 4/2003 | Manasas et al. | 623/17.15 |
| 2005/0015150 A1* | 1/2005 | Lee | 623/17.12 |
| 2005/0080488 A1 | 4/2005 | Schultz | |
| 2005/0165485 A1* | 7/2005 | Trieu | 623/17.13 |
| 2006/0259147 A1* | 11/2006 | Krishna et al. | 623/17.15 |
| 2006/0293752 A1 | 12/2006 | Moumene et al. | |
| 2007/0162137 A1* | 7/2007 | Kloss et al. | 623/17.15 |
| 2007/0225810 A1 | 9/2007 | Colleran et al. | |
| 2008/0161928 A1* | 7/2008 | Trieu | 623/17.16 |
| 2008/0195212 A1* | 8/2008 | Nguyen et al. | 623/17.16 |
| 2009/0076614 A1* | 3/2009 | Arramon | 623/17.16 |

FOREIGN PATENT DOCUMENTS

| | | |
|---|---|---|
| FR | 2877833 | 5/2006 |
| WO | WO2004/019828 | 3/2004 |
| WO | WO2004/054479 | 7/2004 |
| WO | WO2004/071282 | 8/2004 |
| WO | WO2005/041818 | 5/2005 |

* cited by examiner

*Primary Examiner* — Mary Hoffman
(74) *Attorney, Agent, or Firm* — Jennifer S. Stachniak; Robert W. Becker

(57) ABSTRACT

A method of limiting the movability of an intervertebral disk prosthesis with regard to pivoting movements, and an intervertebral disk prosthesis. The method includes the step of asymmetrically limiting at least one of a flexion-extension movement, a lateral bending, and a rotation about a vertical axis in order to limit the movability of the prosthesis. The prosthesis comprises articulated prosthesis components, and movement-limitation measures configured to limit movability of the components with respect to flexion-extension movement, lateral bending and a rotation about a vertical axis of the prosthesis in a defined manner.

12 Claims, 4 Drawing Sheets

INTERVERTEBRAL DISK PROSTHESIS

BACKGROUND OF THE INVENTION

The instant application should be granted the priority dates of Dec. 4, 2007, the filing date of the corresponding German patent application 10 2007 058 304.6, as well as Nov. 6, 2008, the filing date of the International patent application PCT/DE2008/001829 filed Nov. 6, 2008.

The present invention relates to a method for limiting the movability of an intervertebral disk prosthesis with regard to pivoting movements, and also relates to an intervertebral disk prosthesis.

Intervertebral disk prostheses are known where the prosthesis components permit movement in a number of directions, so that a patient having one or more prostheses of this type as an intervertebral disk replacement, to a large extent can maintain his original freedom of movement.

Pursuant to WO 2004/019828 A1, EP 1 124 509 B1, and DE 42 08 116 C2, limitations of the rotation about the vertical axis by means of shaping measures are proposed in that the sliding surfaces for the lateral inclination for bending on the one hand, and for the flexion-extension inclination or bending on the other hand, receive different radii of curvature. However, this entails complicated configurations of the prosthesis components.

In order to be able to imitate the degree of freedom of movement of a natural intervertebral disk, a prosthesis intermediate component is proposed pursuant to DE 103 61 772 A1 that between a cover plate and a face plate can carry out translational and rotational movements relative to the plates. However, with this proposal, movements cannot be limited in an optimal manner.

It is an object of the present invention to develop a method and an intervertebral disk prosthesis with which the movability of the replacement intervertebral disk can, to the greatest extent possible, be optimally adapted to the requirements of a patient.

SUMMARY OF INVENTION

The object is realized by a method of limiting the movability of an intervertebral disk prosthesis with regard to pivoting movements by asymmetrically limiting the flexion-extension movement and/or the lateral inclination or bending and/or the rotation about a vertical axis of the prosthesis. The object is also realized by an intervertebral disk prosthesis that comprises articulated prosthesis components, and movement, lateral bending and rotation of the prosthesis about a vertical axis, all in a defined manner. The ivtervertebral disk prosthesis can further comprise artificial vertebra end plates that are configured to be permanently fixed on vertebra bodies, wherein the end plates are further configured to exchangeably receive the articulated prosthesis components and/or the movement-limitation measures.

The movability of the implant is limited in every direction of movement in a defined manner adapted or tailored for the individual patients, i.e. the flexion-extension movement and/or the lateral inclination or bending and/or the rotation about the vertical axis are limited asymmetrically, and where possible and/or necessary also symmetrically.

With the inventive measures, not only is a good adaptation to the movement possibilities of the individual patient achieved, but rather movement failures can also be better corrected.

Suitable for carrying out the method are the functionally straight forward intervertebral disk prostheses having a ball/socket system that is movable three dimensionally, i.e. is rotatable and pivotable. In a defined manner, for example elastic shock absorbers or cushion blocks having different elastic characteristics for the non-uniform limitation of the extension movement on the one hand, and lateral bending in both directions on the other hand, are used. The fixation of the shock absorbers is effected at the vertebra bodies or on artificial vertebra end plates or apposition plates.

Pursuant to a preferred embodiment, the artificial vertebra end plates are connected with the vertebra bodies, separate from the prosthesis, in such a way that they remain permanently anchored and serve as a mounting support for the prosthesis and the movement-limitation measures. This has the advantage that if exchange or replacement of the prosthesis and/or one or more movement-limitation measures becomes necessary, this implies only one mechanical detachment and reconnection to the artificial vertebra end plates, and not to bones. This facilitates and accelerates the operation process, and also preserves and protects the substance of the bone.

A connection of the shock absorbers on one side, for example on only one of the artificial vertebra end plates or one vertebra body, means that as a consequence these shock absorbers have no impact upon the rotational movement about the vertical axis, so that their limitation can also be selected in a defined manner independently of the flexion movement. For this purpose, for example tension cord bands having different thicknesses or strengths could be used that, fixed on the two artificial vertebra end plates or vertebra bodies in a crossed manner, asymmetrically limit the rotation about the vertical axis toward the right and toward the left, or that are provided with different restoring or elastic forces.

Although the use of elastic shock absorbers is known from DE 203 15 611 U1, involved here are symmetrical elements that exert identical restoring forces onto the deflected prosthesis components independently of the direction of movement.

A straightforward embodiment having elastic elements comprises, pursuant to the invention, a U-shaped shock absorber that is provided with elastic characteristics that differ over the length, and that after the implantation of the prosthesis is laterally inserted between the vertebra bodies and is fixed on prosthesis components, on artificial vertebra end plates or the pertaining vertebra bodies.

The measures that limit movement can, pursuant to a further embodiment of the invention, be achieved by appropriate configurations of the prosthesis components that are movable relative to one another. By way of example of the hemisphere/socket system, this solution can be achieved by assymetrical configurations of the hemisphere and/or of the socket.

The movement-limiting function can also be at least partially assumed by elastic bands, such as tension cord bands, that bridge the intervertebral disk region and generate different tension forces to achieve the necessary precise movement limitations. Depending upon the design of the prosthesis, the bands are secured either to prosthesis components, to artificial vertebra end plates, or on the two adjoining or further vertebra bodies.

The elastic band can preferably accommodate a shock absorber or can be embodied with an integrated shock absorber, whereby the shock absorber is disposed in a non-fixated manner between, for example, vertebra end plates. In this way, a dampening of compression and tension is effected, whereby the movement limitation system can, if necessary, be easily removed and exchanged by merely undoing the screw connection of the elastic band.

Further possible embodiments are comprised in the use of elastic springs having different spring characteristics.

The use of the inventive measures is not limited to ball/socket intervertebral disk prostheses. For example, an intervertebral disk prosthesis comprised of an elastic material that, in a direction-dependent manner, has different elastic characteristics can be disposed directly between two vertebra end plates and is loosely held in a required position by at least one border or apron that is connected with a vertebra end plate. However, the elastic material can also be connected with a vertebra end plate, for example adhesively, while the second vertebra end plate is provided with a border or apron.

In order to achieve the individual effect for the respective patient, pursuant to a further embodiment of the invention a combination of the previously described movement-limitation measures can be utilized.

Pursuant to one advantageous embodiment of the invention, the movement-limitation means is removably secured with prosthesis components, as a result of which during repair operations, the measures, without having to remove the prosthesis itself, can be easily replaced. Such operations are, for example, necessary if a new configuration of the individual movement limitations is required for the patient.

Pursuant to a further embodiment of the invention, artificial vertebra end plates are provided that are respectively permanently fixated on one of the adjoining vertebra bodies by means of adhesion, screw connections, staples, etc. The articulated prosthesis components, and possibly the movement-limitation measures, are removably secured with the vertebra end plates, for example via a screw connection. In this way, a post operation, with which the prosthesis components or movement-limitation measures must be replaced or exchanged, is reduced to a mechanical exchange of the elements. Thus, with a repair operation the prosthesis module and/or the movement-limitation measures are exchanged, while the artificial vertebra end plates remain in the implanted state. Consequently, the material of the bone is protected, and a repair operation is significantly easier and takes less time.

Standardized vertabra end plates offer a further advantage, with such end plates being associated with standardized prosthesis modules of differing design configuration and types. For example, a straightforward type exchange is possible if, for example, for a patient an exchange of the originally inserted articulated prosthesis components for a different design or configuration is necessary.

BRIEF DESCRIPTION OF THE DRAWINGS

The invention will be explained in greater detail with the aid of embodiments schematically illustrated in the drawings, in which.

DESCRIPTION OF SPECIFIC EMBODIMENTS

Figure 1:
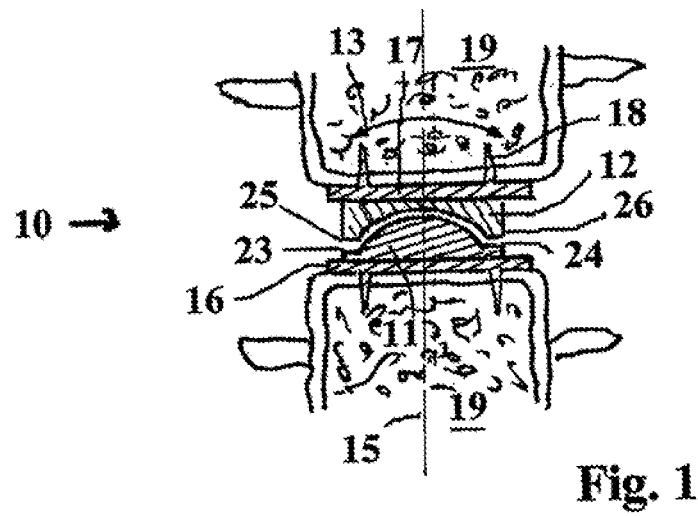
FIG. 1 is a cross-sectional dorsal view of two vertebra bodies and an intervertebral disk prosthesis having hemisphere/socket technology.

FIG. 1 is a longitudinal cross-sectional view showing an intervertebral disk prosthesis 10 comprised of a hemisphere or ball 11 and a socket 12 that cooperates therewith. The hemisphere 11 and the socket 12 are respectively carried by a vertebra end plate 16 or 17 respectively, which in turn are connected with the respective vertebra body 19 via pins or staples 18. A prosthesis of this type is articulated in a three-dimensional manner, being movable in lateral inclination or bending 13, rotation 21 about the vertical axis 15, and also permitting the flexion-extension movement 14 illustrated in FIG. 2.

In order to restrict the free movability of the prosthesis to the needs of the patient, measures are undertaken that individually limit each of the three directions of movement 13, 14 and 21.

Pursuant to FIG. 1, a profiling measure is shown that more greatly limits the lateral bending, for example toward the right, than toward the left. For this purpose, the hemisphere 11 is formed on the left side with a lower step 23, and on the right side with a higher step 24, so that when the patient carries out a lateral bending 13, the left socket edge 25 can execute a longer displacement than can the right socket edge 26. To avoid damage and severe impact, the steps 23, 24 and/or the socket edges 25, 26 can be coated with non-illustrated elastic coatings.

In a similar manner, steps of this type can be provided in the plane perpendicular to the drawing plane of FIG. 1 for limiting the flexion-extension movement.

It is quite possible with patients that the movability of an implanted intervertebral disk replacement or prosthesis must be altered during the course of time. It is therefore advantageous for an intervertebral disk prosthesis having limitation means to have a modular construction where artificial vertebra end plates 16, 17 are permanently connected with the vertebra bodies 19, and the hemispheres 11 as well as the sockets 12 are removably (not illustrated in FIG. 1) secured to the artificial vertebra end plates 16, 17. For this purpose, bayonette or dove-tailed connections can be provided between articulation modules 11, 12 and artificial vertebra end plates 16, 17. Alternatively, the vertebra end plates 16, 17 can be equipped with screw holes for this purpose.

Figure 2:
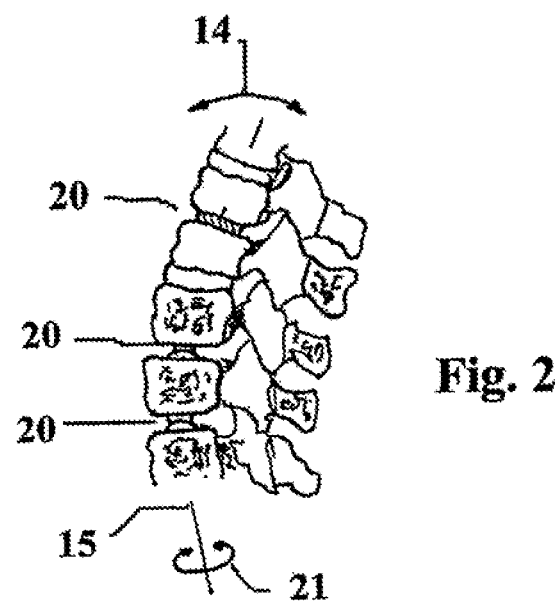
FIG. 2 is a side view of a spine or vertical column having a plurality of intervertebral disk prostheses, and FIGS. 3-6b each show a further embodiment of the invention.

FIG. 2 is merely a side view of a spine or vertebral column having a plurality of intervertebral disk prostheses 20.

Figure 3A:
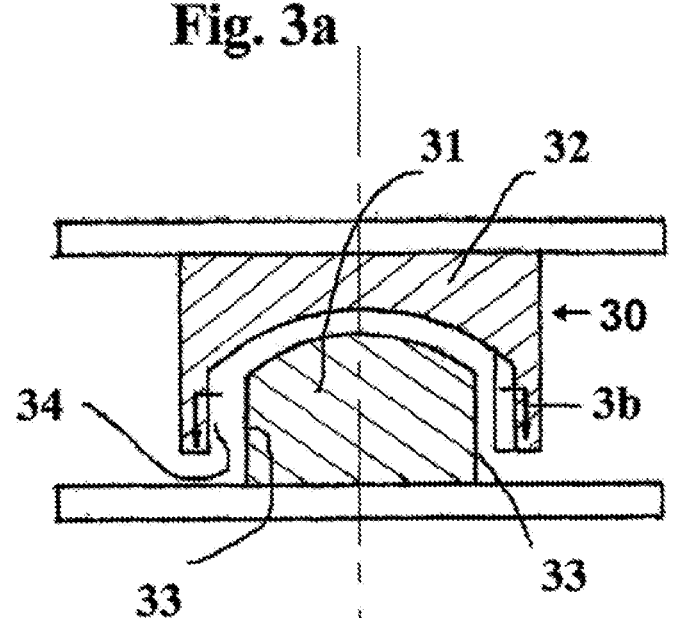
Figure 3B:
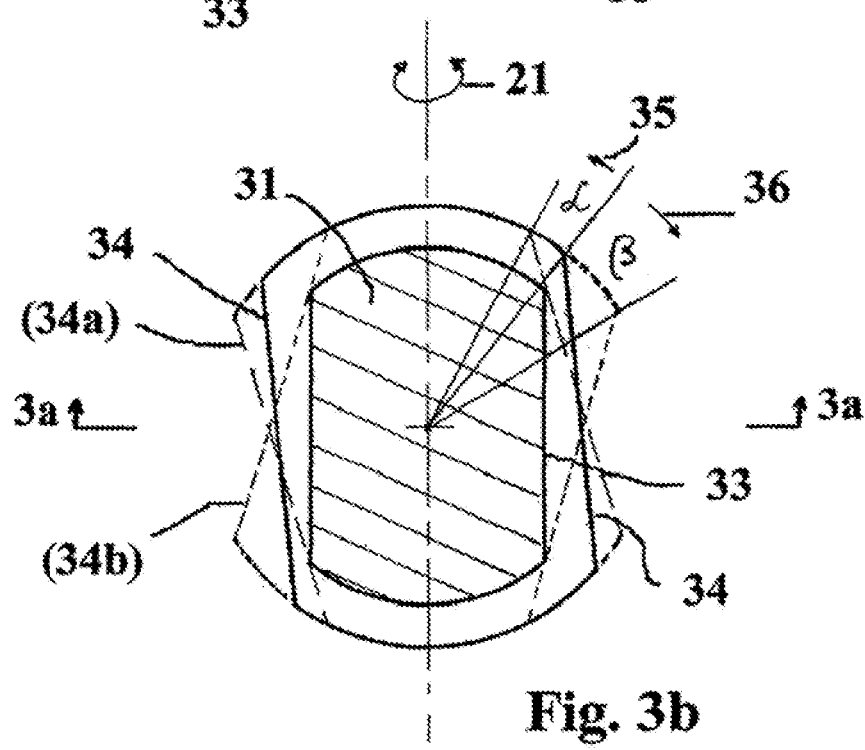

A profiling, asymmetrical measure for limiting the rotational movement 21 is illustrated in FIG. 3a in a partial longitudinal section and in FIG. 3b in a cross-section. The hemisphere or ball 31 of the intervertebral disk prosthesis 30 has two parallel flattened portions 33, and the socket 32 has planar narrowed portions 34 that extend parallel to one another and that, however, in the position of rest of the prosthesis 30 extend at an angle to the flattened portions 33 of the hemisphere. This state of rest is illustrated in FIG. 3b by the solid lines of the narrow portions 34. Consequently, the rotational movability 21 is reduced by a predetermined amount due to a positive engagement. The inclined positions of the planar surfaces 33 and 34 relative to one another effect different maximum angles of rotation $\alpha$, $\beta$ toward the left or toward the right respectively. If the patient turns toward the left (arrow 35) the prosthesis permits a smaller angle of rotation a than toward the right (arrow 36, angle $\beta$). The positions of the sockets 32 in the rotational movement limitations 34a and 34b are illustrated by dashed lines in FIG. 3b.

Movement limitations brought about by a positive engagement are not limited to the embodiments described here. Any other configuration, tongue and groove, projections, etc., that are suitable for limiting the movability is the subject matter of this invention. Similarly, the invention is not limited to intervertebral disk prostheses in the ball/hemisphere-socket technology. The invention can be illustrated in a particularly straightforward manner with this exemplary embodiment.

Figure 4:
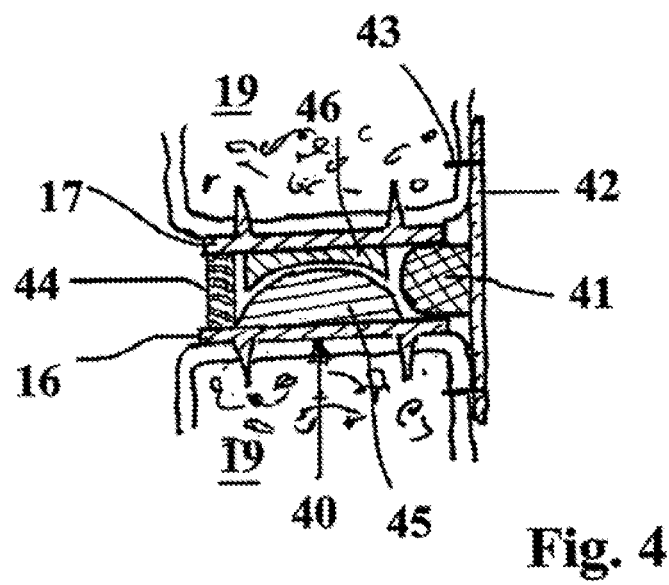
Figure 5:
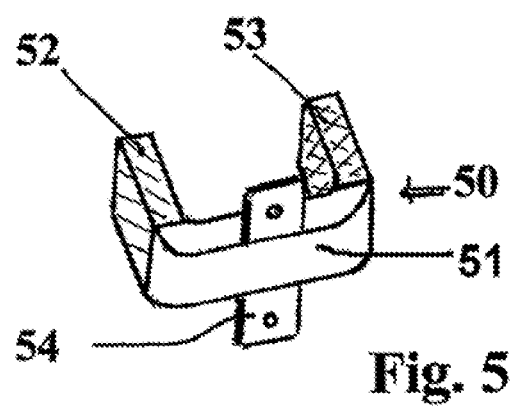

An embodiment having elastic movement-limitation measures is shown in FIG. 4 and in FIG. 5. FIG. 4 shows an intervertebral disk prosthesis 40 having a cushion or shock absorber 41 that on one side of the prosthesis 40 extends in between the artificial vertebra end plates 16, 17 and is held via an elastic band 42 that is secured to the vertebra bodies 19 via screws 43. Illustrated on the opposite side of the prosthesis 40, as a further example, is a tension and/or compression spring 44.

Generally, either shock absorbers 41 or springs 44 having the same or different elastic properties are utilized on both sides. However, it is, of course, also possible to utilize different limitation measures, as illustrated by way of example in FIG. 4. The elastic band 42, such as, for example, a tension cord band, is similarly incorporated for the limitation of movement, and, instead of being fixated on the vertebra bodies 19 via the screws 43, can be fixated on the artificial vertebra end plates 16, 17.

Shock absorbers 41 and springs 44, disposed across from one another on both sides of the articulation components 45, 46, serve for the limitation of the flexion-extension movement or the lateral bendings. In order to limit both directions of movement, such or similar measures are similarly provided in the plane transverse to the plane of the drawing sheet, whereby all or only two oppositely disposed measures have different properties for the unequal limitation of movement. The springs 44, which are connected with the vertebra end plate 16, 17, and the elastic band 42 also exert tension forces, which are incorporated into the design of the movability.

By means of the elasticity of the shock absorber 41, when this is connected with the connection plates 16, 17, for example by adhesion, and the tension force of the band 42, the rotational movability is additionally held within limits. With an appropriate design, and via the shearing forces, the springs 44 can also exert a defined influence upon the rotation about the vertical axis.

The plates 16, 17 can also be viewed as artificial vertebra end plates 16, 17 that are separate from the articulation prosthesis 45, 46, and that are disposed on the vertebra bodies in such a way that they remain permanently implanted and serve as support for diverse components. In this case, instead of being screwed to vertebrae, the tension cord band can be screwed onto the artificial vertebra end plates 16, 17. It is to be understood that in such a case, the articulation components 45, 46 of the prosthesis 40 are also removably connected to the artificial vertebra end plates 16, 17.

It is expedient, if the measures 41, 42, 44, 50 that are separate for the movement limitation, as shown in FIGS. 4 and 5, are used, for them to additionally be removably connected with artificial vertebra end plates 16, 17. If a change of the movability becomes necessary, then in a further surgical operation it is merely necessary to exchange the measures 41, 42, 44, 50 by removing the measures that are to be replaced or exchanged from the artificial vertebra end plates 16, 17, and to insert the new measures and secure them thereto, without having to replace the entire intervertebral prosthesis 40.

Instead of a plurality of shock absorbers, a single shock absorber 50, that at least partially surrounds the articulation location 45, 46 of the intervertebral disk prosthesis 40, represents a straightforward measure for limiting movement. One exemplary embodiment for accomplishing this is represented in FIG. 5, and comprises a U-shaped shock absorber 50 that from the operation side is inserted between the artificial vertebra end plates 16, 17 and is screwed to the side edges of the connecting plates 16, 17 by means of attachment noses or tabs 54. The geometry of the approximately U-shaped shock absorber 50 is adapted to the intervertebral disk prosthesis, e.g. semicircular elastic shock absorbers are possible. In order to be able to have a varying influence upon the movability in different directions, the shock absorber 50 is provided with different characteristics over its length. For example, the legs 52 and 53 of the U-shaped shock absorber 50 can be provided with elastic characteristics that differ from those of the connecting member 51 or even from one another.

Figure 6A:
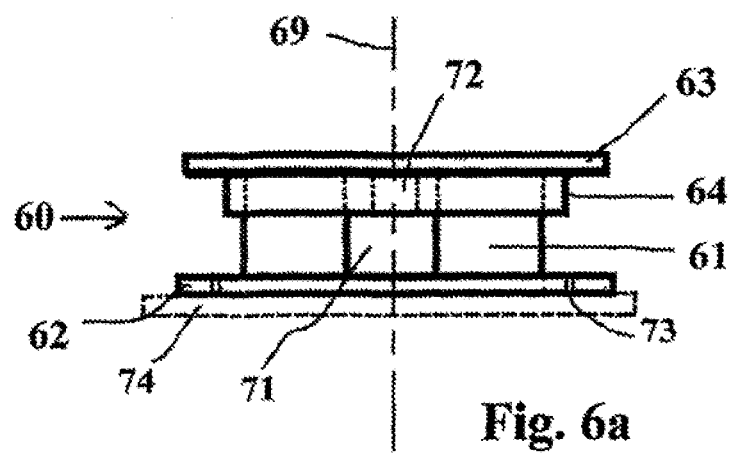
Figure 6B:
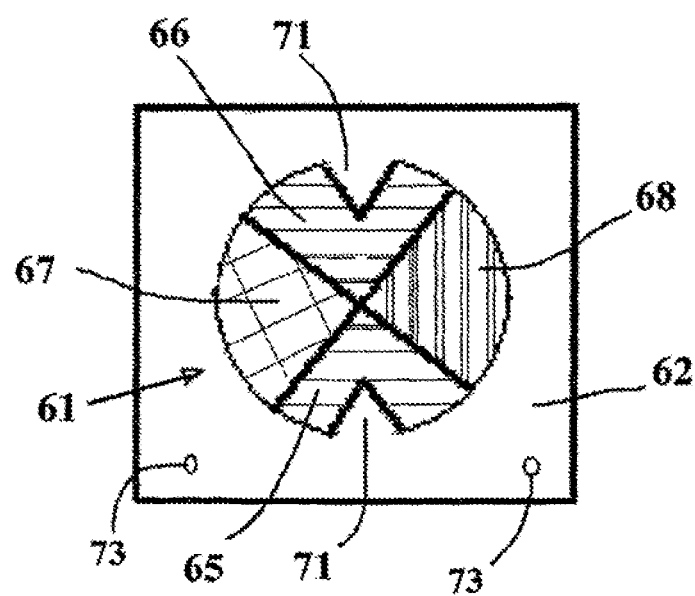

FIGS. 6a and 6b are a side view and a cross-section respectively of an exemplary embodiment where the intervertebral disk prosthesis 60 is essentially comprised of an elastic cylinder 61, which is connected with the lower plate 62, for example adhesively. The upper plate 63 is provided with a collar-shaped apron 64 that extends around the elastic cylinder 61 in a centering manner.

The elastic cylinder 61 is comprised of four sectors 65-68 having different elastic characteristics, whereby for example for the lateral bending two oppositely disposed sectors 65, 66 with the same characteristics are provided. For the differing limitation of the flexion and extension movement, the two remaining sectors 67, 68 are provided with different elastic characteristics. A number of different material pairings having polymeric materials, metal, ceramic, or combinations thereof are also possible.

To limit the rotation about the vertical axis 69, a respective wedge-shaped groove 71 is disposed parallel to the vertical axis 69 in opposite sectors 65, 66, whereby a respective wedge-shaped nose 72 on the inner side of the apron extends into the grooves with appropriate play. Instead of the wedge shape, any other shape can be selected, for example groove and nose having a quadratic cross-section.

The exemplary embodiment pursuant to FIG. 6 can be varied such that, for example, the upper plate 63 with the apron 64, to form a structural component, is anchored as an artificial vertebra end plate 63, 64 on the vertebra body, and serves as a mounting support. Also permanently anchored on the opposite vertebra body is a planar vertebra end plate 74, which is illustrated in dashed lines. The prosthesis component 61, 62 is inserted between the two vertebra end plates 63, 64, and is removably connected with the lower artificial vertebra end plate 74. For this purpose, for example, inclined bores 73 are provided in the plate-shaped prosthesis component 74, and non-illustrated inclined bores are provided in the artificial vertebra end plate 74, all for a screw connection.

The artificial vertebra end plate 63, 64 and 74, which serve as mounting supports, can accommodate further elements, for example for limiting movement, that are similarly mounted in a removable fashion. In the exemplary embodiment of FIG. 6, the rotation about the vertical axis 69 can also be limited, for example, by elastic bands, which are appropriately screwed to the two artificial vertebra end plates 63, 64 and 74. In this case, the grooves 71 and noses 72 are eliminated.

The specification incorporates by reference the disclosure of German 10 2004 054 121.3 filed Nov. 8, 2004, as well as International application PCT/EP2005/009395, filed Sep. 1, 2005.

The present invention is, of course, in no way restricted to the specific disclosure of the specification and drawings, but also encompasses any modifications within the scope of the appended claims.

The invention claimed is:

1. A method of limiting the movability of an intervertebral disk prosthesis with regard to pivoting movements, including the step of:

asymmetrically limiting at least one of a flexion-extension movement, a lateral bending, and a rotation about a vertical axis of an intervertebral disk prosthesis in order to limit the movability of said prosthesis, wherein said asymmetrically limiting step comprises first permanently fixing artificial vertebral end plates on adjoining vertebral bodies, and removably connecting at least one of said intervertebral disk prosthesis in the form of an articulated intervertebral disk prosthesis and measures for asymmetrical movement limitation with said artificial vertebral end plates, wherein said movement-limitation measure is an approximately U-shaped shock absorber that has different elastic characteristics over its length; and carrying out alternations of movablilty limitations during a repair operation in such a way that said measurements for asymmetrical limitation of movability are removed from said artificial vertebral end plates and are replaced by new ones that are removably connected with original ones of vertebral end plates.

2. A method according to claim 1, which includes the further step of using a ball-socket system as said intervertebral disk prosthesis, wherein said ball-socket system is provided with means for an asymmetrical limitation of the movability.

3. A method according to claim 1, wherein at least one elastic band is attached to at least one of the group consisting of at least two vertebral bodies and said vertebral end plates to limit tension movement.

4. An intervertebral disk prosthesis comprising:
articulated prosthesis components,
movement-limitation measures configured to asymmetrically limit movability of said components with respect to at least one of a flexion-extension movement, a lateral bending and a rotation about a vertical axis of said prosthesis in a defined manner, and
artificial vertebral end plates that are configured to be permanently fixed on vertebral bodies, wherein said artificial vertebral end plates are further configured to exchangeably receive at least one of said articulated prosthesis components and said movement-limitation measures, wherein said movement-limitation measure is an approximately U-shaped shock absorber that has different elastic characteristics over its length, and wherein said movement-limitation measures are removably secured with said articulated prosthesis components.

5. An intervertebral disk prosthesis according to claim 4, wherein said movement-limitation measures are realized by means of configuration of said prosthesis components.

6. A intervertebral disk prosthesis according to claim 4, wherein said movement-limitation measures are recessed areas or grooves that form a positive or interlocking connection.

7. An intervertebral disk prosthesis according to claim 4, wherein said movement-limitation measures are elastic movement-limitation measures, such as shock absorbers or cushion blocks, or springs, having different elastic characteristics.

8. An intervertebral disk prosthesis according to claim 4, which further comprises at least one elastic band that is configured to be secured to at least two vertebral bodies and that exerts tension forces.

9. An intervertebral disk prosthesis according to claim 8, wherein said at least one elastic band is configured for accommodation and partial fixation of intervertebral disk prostheses or components thereof.

10. An intervertebral disk prosthesis according to claim 4, wherein said movement-limitation measures at least partially include tension cord bands.

11. An intervertebral disk prosthesis according to claim 4, wherein said movement-limitation measures include a combination of different movement-limitation measures.

12. An intervertebral disk prosthesis according to claim 4, wherein said artificial vertebral end plates are standardized vertebral end plates.

\* \* \* \* \*